(12) United States Patent
Palmer

(10) Patent No.: US 10,265,500 B2
(45) Date of Patent: *Apr. 23, 2019

(54) COMPACT PACKAGED INTERMITTENT URINARY CATHETER

(71) Applicant: Cure Medical LLC, Newport Beach, CA (US)

(72) Inventor: Timothy A. Palmer, Stillwater, MN (US)

(73) Assignee: Cure Medical LLC, Newport Beach, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/707,817

(22) Filed: Sep. 18, 2017

(65) Prior Publication Data

US 2018/0001053 A1 Jan. 4, 2018

Related U.S. Application Data

(63) Continuation of application No. 15/094,749, filed on Apr. 8, 2016, now Pat. No. 9,764,112, which is a
(Continued)

(51) Int. Cl.
*A61M 5/32* (2006.01)
*A61M 25/00* (2006.01)
(Continued)

(52) U.S. Cl.
CPC ...... *A61M 25/002* (2013.01); *A61M 25/0017* (2013.01)

(58) Field of Classification Search
CPC ........... A61M 5/32; A61M 27/00; A61F 5/44; B65D 83/10; B65D 81/02
See application file for complete search history.

(56) References Cited

U.S. PATENT DOCUMENTS 3,345,988 A 10/1967 Vitello
3,556,294 A 11/1971 Walck et al.
(Continued)

FOREIGN PATENT DOCUMENTS

AT 369994 B 2/1983
EP 0677299 B1 7/2001
(Continued)

OTHER PUBLICATIONS

180° Medical, Inc., Intermittent Catheters, website article, first published in 2013, https://www.180medical.com/Intermittent-Catheters, last accessed Apr. 7, 2016.

*Primary Examiner* — Andrew J Mensh
*Assistant Examiner* — Ilya Y Treyger
(74) *Attorney, Agent, or Firm* — SoCal IP Law Group LLP; Guy Cumberbatch; Steven Sereboff

(57) ABSTRACT

A compact packaged intermittent urinary catheter having a longitudinally elongated intermittent urinary catheter retained within a longitudinally compacted elastic package. A method of using the catheter wherein at least a portion of the package is used as a drainage tube for the catheter. A package for an intermittent urinary catheter including a longitudinally compacted elastic package having a longitudinally extending receiving chamber containing a lubricating medium. The package having two longitudinal ends that may be removed to open the package and enable conversion of the package from a compacted state to an extended state. A method of using the package as a clean handling sleeve through which an intermittent urinary catheter may be passed to coat it with a lubricating medium.

20 Claims, 18 Drawing Sheets

Related U.S. Application Data continuation-in-part of application No. 13/790,495, filed on Mar. 8, 2013, now Pat. No. 9,694,157.

(51) Int. Cl.
    *A61M 27/00*      (2006.01)
    *A61F 5/44*      (2006.01)
    *B65D 83/10*      (2006.01)
    *B65D 81/02*      (2006.01)

(56) References Cited

U.S. PATENT DOCUMENTS

| | | | |
|---|---|---|---|
| 3,898,993 A | 8/1975 | Taniguchi | |
| 4,141,399 A | 2/1979 | Zoland | |
| 5,242,428 A | 9/1993 | Palestrant | |
| 5,623,940 A | 4/1997 | Daikuzono | |
| 6,053,905 A | 4/2000 | Diagnault, Jr. et al. | |
| 6,402,726 B1 | 6/2002 | Genese | |
| 6,544,240 B1 | 4/2003 | Borodulin et al. | |
| 7,334,679 B2 | 2/2008 | Givens, Jr. | |
| 7,682,353 B2 | 3/2010 | Tanghoj et al. | |
| 8,181,778 B1 | 5/2012 | van Groningen et al. | |
| 8,910,828 B2 | 12/2014 | Kanderka et al. | |
| 2009/0024111 A1 | 1/2009 | Borodulin et al. | |
| 2009/0054876 A1 | 2/2009 | Borodulin et al. | |
| 2009/0204106 A1 | 8/2009 | Golden | |
| 2011/0046571 A1 | 2/2011 | Waldhorn | |
| 2011/0114520 A1 | 5/2011 | Matthison-Hansen | |
| 2012/0271282 A1 | 10/2012 | Schertlger | |
| 2013/0327664 A1 | 12/2013 | Tanghoj | |

FOREIGN PATENT DOCUMENTS

| | | |
|---|---|---|
| EP | 2072075 A1 | 6/2009 |
| EP | 2609956 A1 | 7/2013 |
| ES | 2074030 A1 | 8/1995 |
| IL | 56551 A | 2/1982 |
| WO | 1998006642 A1 | 2/1998 |
| WO | 2011011023 A1 | 1/2011 |
| WO | 2011019359 A1 | 2/2011 |
| WO | 2013158270 A1 | 10/2013 |

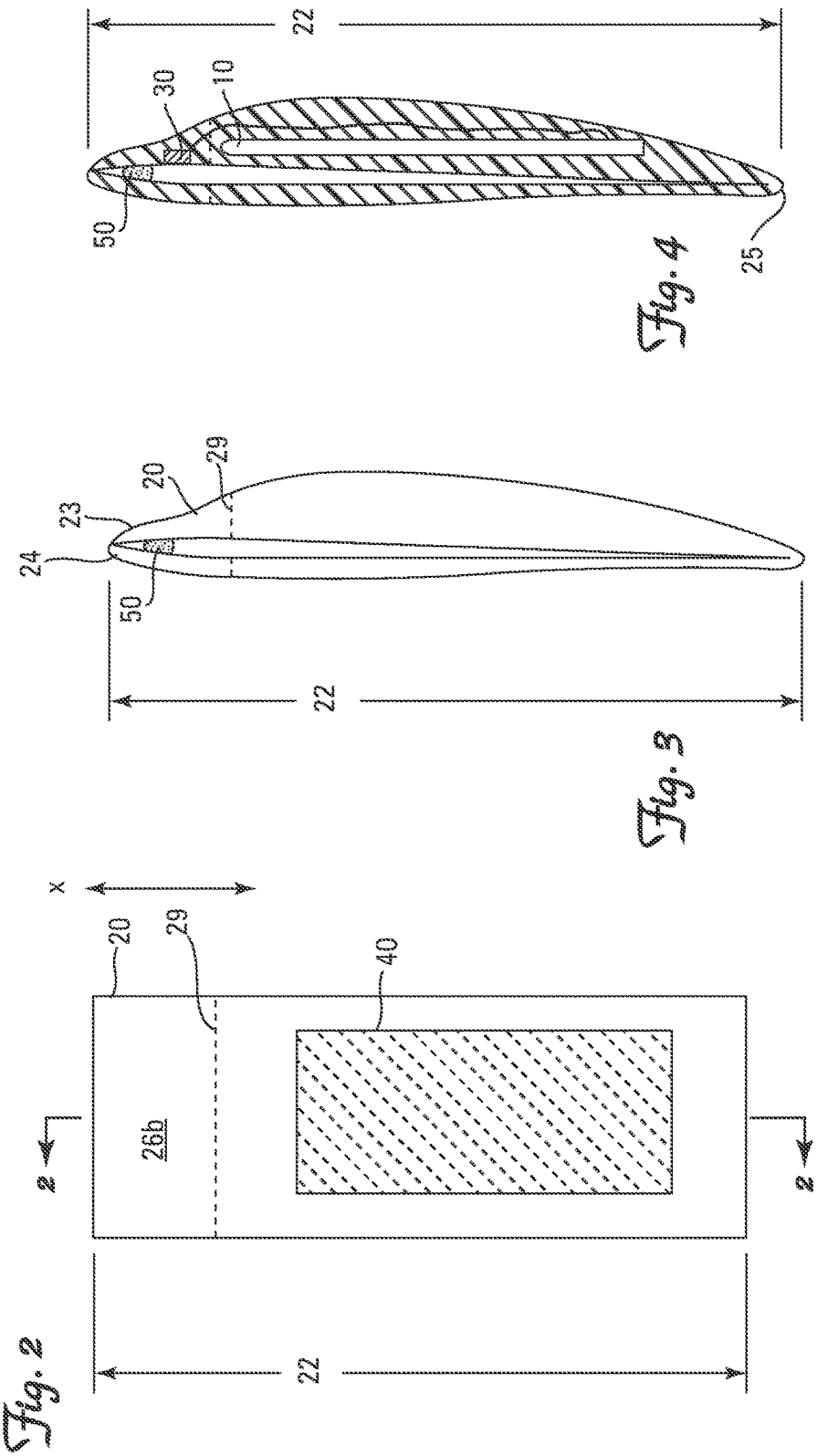

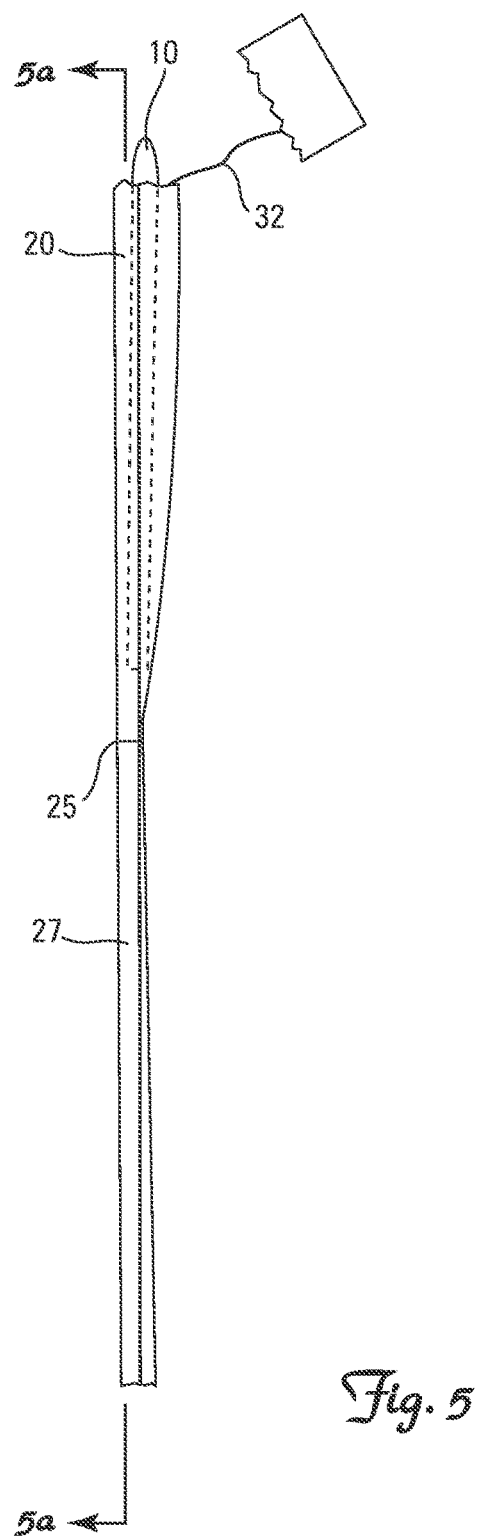

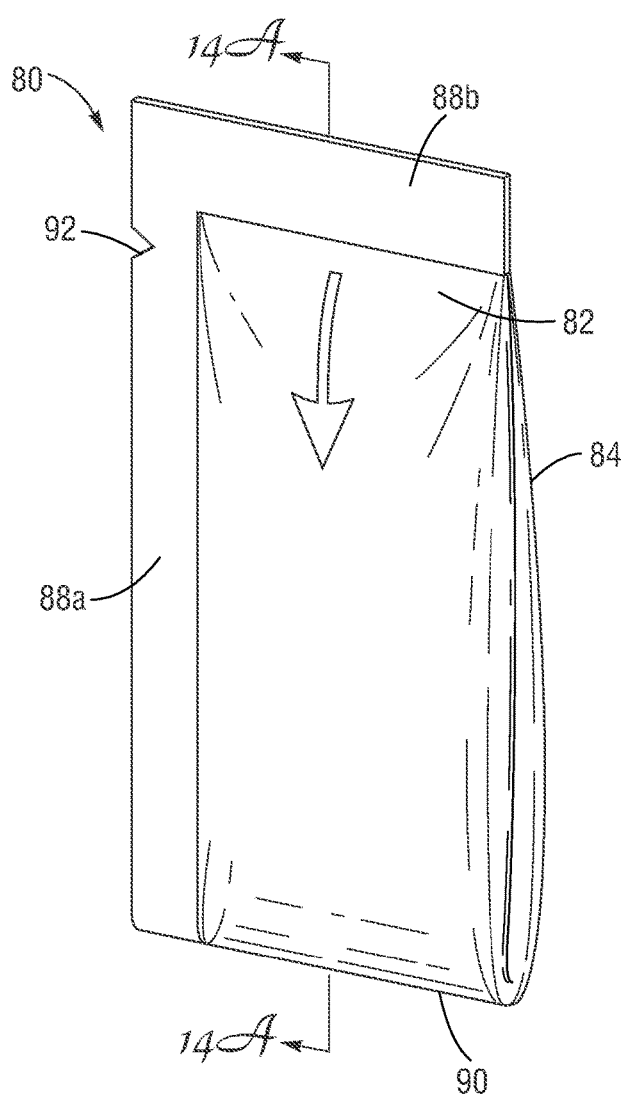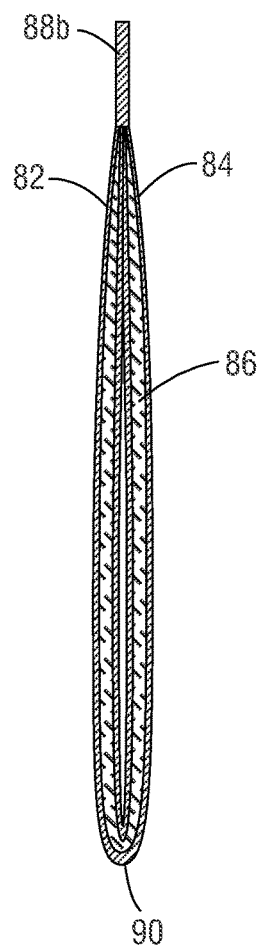

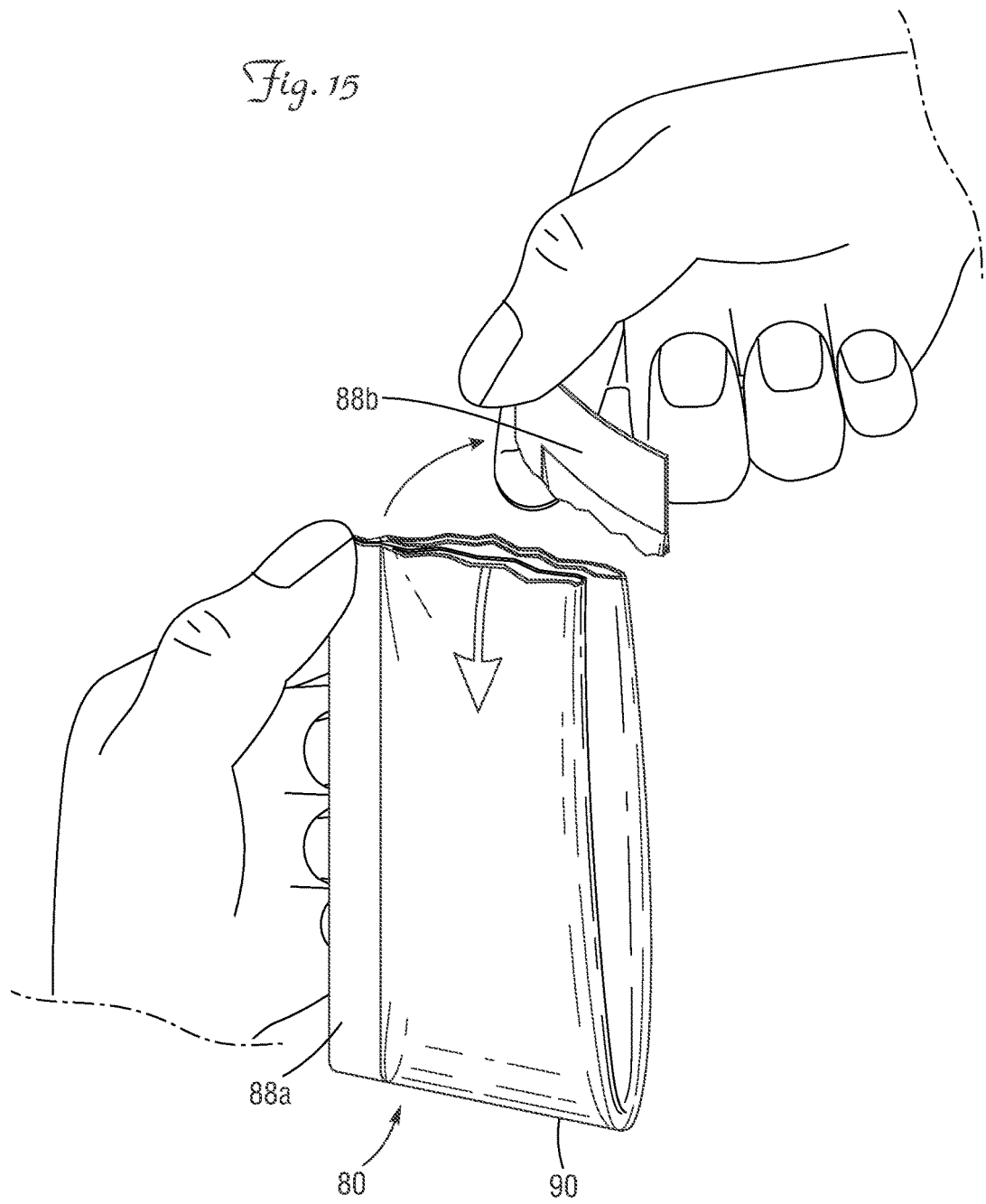

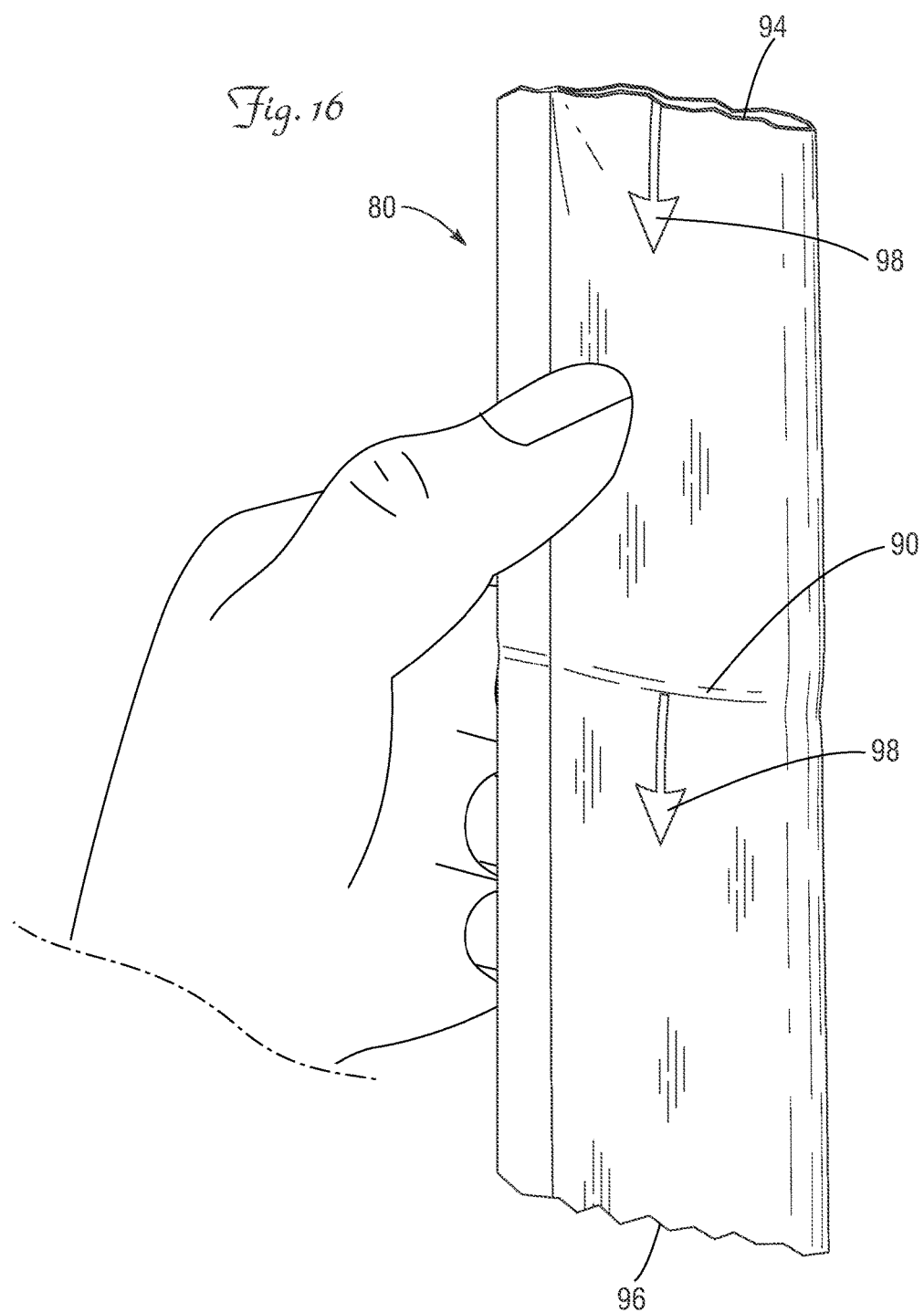

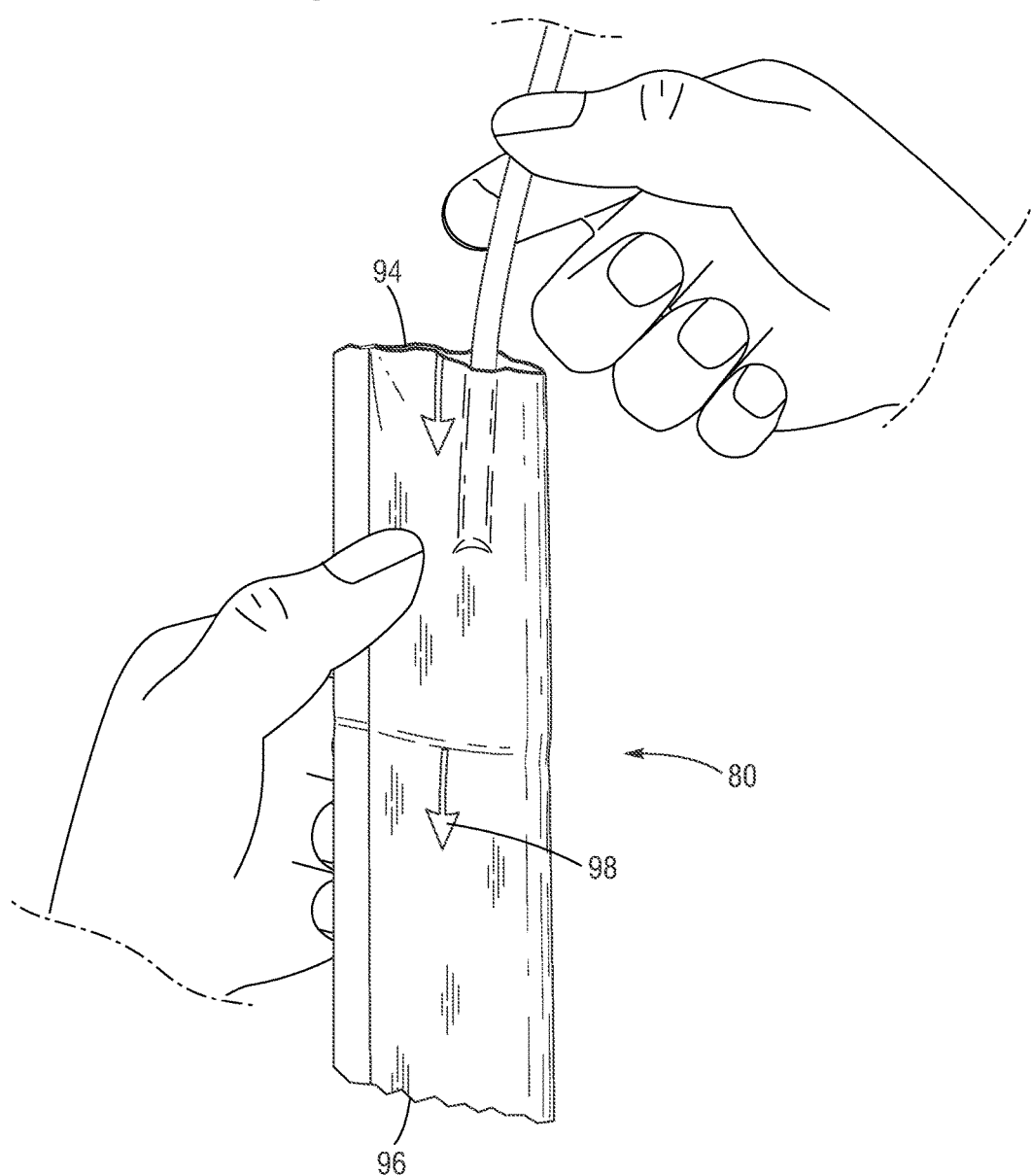

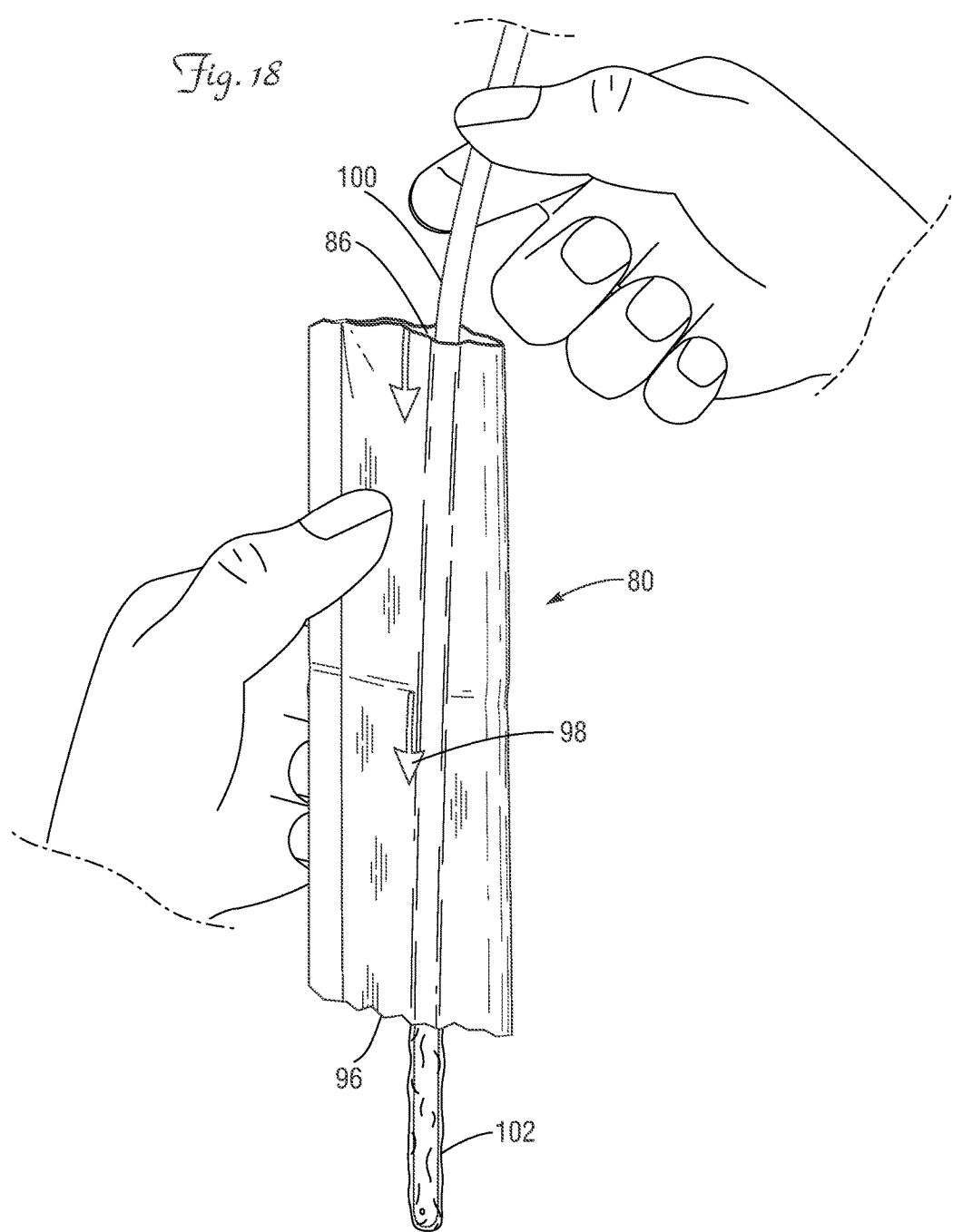

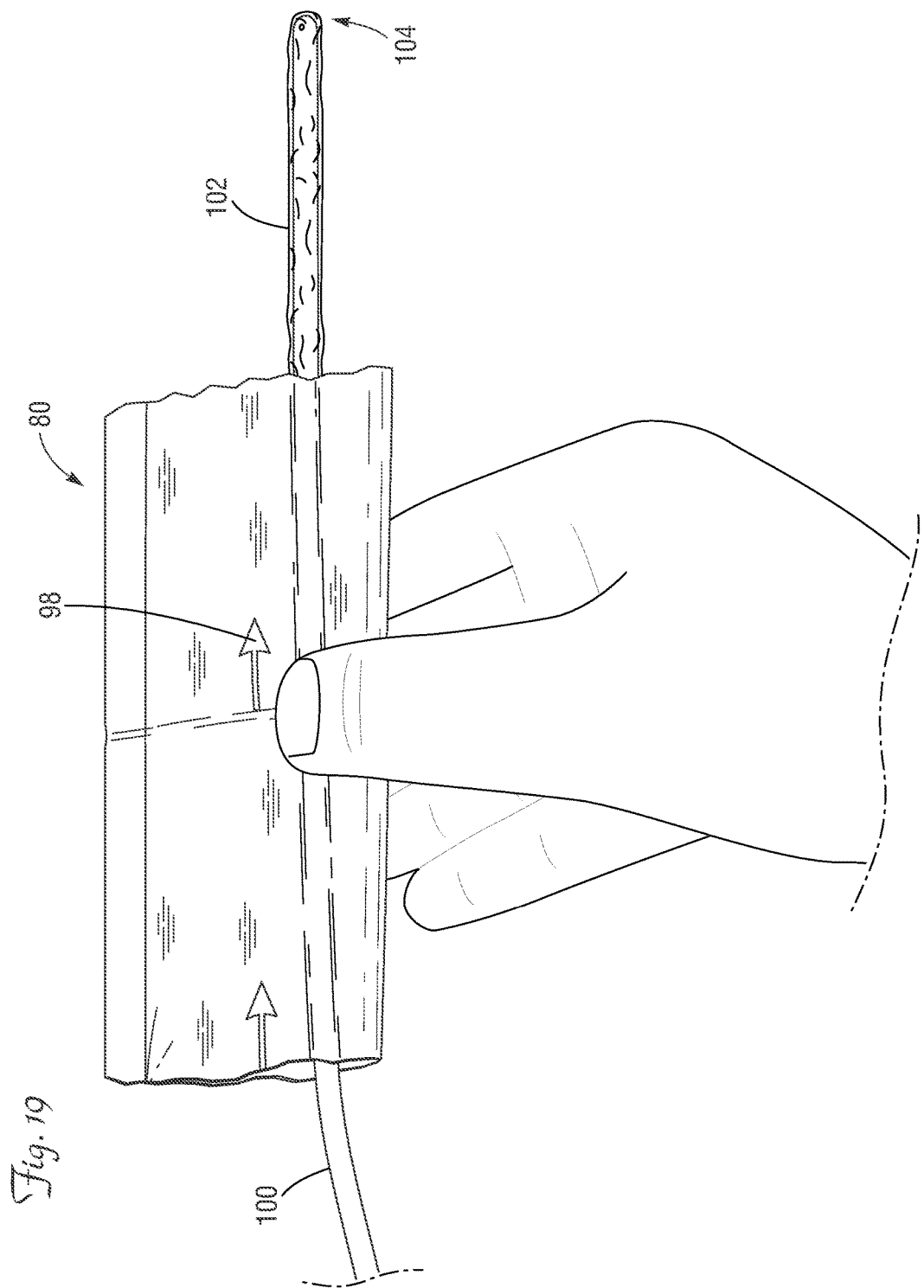

COMPACT PACKAGED INTERMITTENT URINARY CATHETER

RELATED APPLICATION INFORMATION

This patent is a continuation of application Ser. No. 15/094,749 filed Apr. 8, 2016 now U.S. Pat. No. 9,764,112, which is a continuation-in-part of application Ser. No. 13/790,495 filed Mar. 8, 2013 and now issued as U.S. Pat. No. 9,694,157, both titled "COMPACT PACKAGED INTERMITTENT URINARY CATHETER", all of which are incorporated herein by reference in their entirety.

NOTICE OF COPYRIGHTS AND TRADE DRESS

A portion of the disclosure of this patent document contains material which is subject to copyright protection. This patent document may show and/or describe matter which is or may become trade dress of the owner. The copyright and trade dress owner has no objection to the facsimile reproduction by anyone of the patent disclosure as it appears in the Patent and Trademark Office patent files or records, but otherwise reserves all copyright and trade dress rights whatsoever.

BACKGROUND

Intermittent catheters are typically used by patients suffering from urinary incontinence or by individuals unable to have voluntary urination. In our highly mobile culture, the ability to have the freedom to leave home for the day or longer is an important part of life. To accommodate this need single use catheters have been developed to allow patients to perform self catheterization. These catheters and their drainage tubes typically have a considerable length and are packaged in an elongated condition. It can require a considerable amount of space to store and transport enough catheters to accommodate a day long outing.

U.S. Pat. No. 7,682,353 B2 discloses an intermittent catheter kit that provides a catheter in short sections to be assembled at the time of use, but many users of the catheters have limited dexterity to assemble these catheters and may still need drainage tubes to reach a waste receptacle. A need still exists for an easy to use intermittent catheter that is compact and completely assembled upon opening the package.

SUMMARY OF THE INVENTION

A first aspect of the invention is a compact packaged intermittent urinary catheter. The catheter has a longitudinally elongated intermittent urinary catheter retained within a longitudinally compacted elastic package.

In a preferred embodiment the compacted package is folded or coiled such that removal of one end of the package removes the other end of the package.

A second aspect of the invention is a method of using a catheter in accordance with the first aspect of the invention. The method includes the steps of (a) obtaining a compact packaged intermittent urinary catheter retained within a longitudinally compacted elastic package having a first longitudinal end and a second longitudinal end, (b) manually opening the first and second longitudinal ends of the package, (c) returning the package to a full longitudinal length, (d) removing a portion of the catheter from the package and inserting it into a urethra, and (e) using at least a portion of the package as a drainage tube for the catheter.

A further aspect comprises a compact package for an intermittent urinary catheter. The package is longitudinally compacted and elastic and has an open extended state and a closed compacted state. The package further defines a longitudinally extending receiving chamber containing a lubricating medium. The package is sized and configured when in its compacted state such that a first longitudinal end of the package and a second longitudinal end of the package are aligned and attached together and removal of the first longitudinal end causes removal of the second longitudinal end and opening of the package. Also, removal of both first and second longitudinal ends permits the package to be converted to its extended state with both first and second longitudinal ends being open. The longitudinally extending receiving chamber is sized and configured when the package is in its open extended state to slidably receive a longitudinally elongated intermittent urinary catheter so that the lubricating medium coats the catheter exterior.

The compact package may be made from polyester, polyethylene, or a combination of the two materials. A line of weakness proximate the first longitudinal end of the package and the second longitudinal end of the package may be provided wherein the lines of weakness are aligned when the first longitudinal end of the package and the second longitudinal end of the package are aligned and attached together. Preferably, the compacted state of the package includes a single fold with the first and second longitudinal ends being joined together opposite the fold. Alternatively, the compacted state of the package includes a coiled configuration. The compact package may have a hinge to allow the package to be configured and arranged into its compacted state.

Additionally, the compact package may have at least one set of laterally extending dimples configured and arranged to allow the package to be folded into its compacted state. The compact package may also have a biasing means configured and arranged to bias the package toward its extended state, such as a polymer member or at least one pressurized chamber.

A method of using an intermittent urinary catheter is also described including the steps of:
  a. obtaining, in its closed compacted state, the package for an intermittent urinary catheter as set forth in claim 1;
  b. simultaneously removing the first and second longitudinal ends of the package so that both first and second longitudinal ends are open;
  c. converting the package to its extended state;
  d. inserting a leading end of an intermittent urinary catheter into the open first longitudinal end and passing the catheter through the longitudinally extending receiving chamber so that the leading end projects from the open second longitudinal end with lubricating medium coating an exterior surface thereof;
  e. inserting the catheter leading end into a urethra; and
  f. using at least a portion of the package as a clean handling sleeve for the catheter.

The package preferably includes a single fold with the first and second longitudinal ends being joined together opposite the fold, and the step of converting the package to its extended state comprises unfolding the package.

BRIEF DESCRIPTION OF THE DRAWINGS

FIG. 2 is a front plan view of the package in FIG. 1 shown with the package in compact longitudinal length.

FIG. 3 is a side plan view of the package in FIG. 2

FIG. 4 is a cross-sectional side view of the package shown in FIG. 2 taken along line 2-2.

FIG. 5 is a side plan view of the package shown in FIG. 1 with the first and second longitudinal ends removed.

FIG. 14 is a front perspective view of an alternative form of a package to receive and lubricate an intermittent urinary catheter in compact longitudinal length.

FIG. 14A is a cross-sectional side view of the package shown in FIG. 14 taken along line 14-14.

FIG. 15 is a perspective view of the package shown in FIG. 14 with the first and second longitudinal ends removed by a user and in a compact longitudinal length.

FIG. 16 is a perspective view of the package of FIG. 14 after removal of the first and second longitudinal ends and in full longitudinal length.

FIG. 17 is a perspective view of the package of FIG. 14 after removal of the first and second longitudinal ends and in full longitudinal length showing a user inserting an intermittent urinary catheter therein.

FIG. 18 is a perspective view like FIG. 17 showing the intermittent urinary catheter passing completely through the package.

FIG. 19 is a perspective view like FIG. 18 showing the user holding the package with the intermittent urinary catheter therein in preparation for use.

DETAILED DESCRIPTION OF A PREFERRED EMBODIMENT

Nomenclature: 10 Catheter; 11 Distal end; 12 Proximal end; 12a Push block; 13 Longitudinal length; 14 Eyelet; 20 Package; 21 Full longitudinal length; 22 Compact longitudinal length; 23 First longitudinal end; 24 Second longitudinal end; 25 Hinge [0038; 26a Inner surface; 26b Outer surface; 27 Edge; 28 Receiving chamber; 28a Longitudinal length; 28b Shoulder; 29 Line of weakness; 30 Guide member; 31 Tab; 32 Tether; 40 Mirror; 50 Fastener; 60 Dimple; 70 Biasing means; X Longitudinal direction; Y Lateral direction.

Definitions

As utilized herein, including the claims, the phrase "full longitudinal length" means longitudinal length from the first end of the package to the second end of the non-compacted package.

As utilized herein, including the claims, the phrase "compact longitudinal length" means longitudinal length of the compacted package that is less than the full longitudinal length.

As utilized herein, including the claims, the term "compacted" means folded, coiled, pleated, concertina, bent.

As utilized herein, including the claims, the term "elastic" means able to resume to proximate normal shape spontaneously after bending, coiling, pleating, or other form of distortion.

Description

Construction

The invention is a longitudinally elongated intermittent urinary catheter 10 packaged in a longitudinally compacted elastic package 20 and a method of using the catheter 10.

Figure 1:
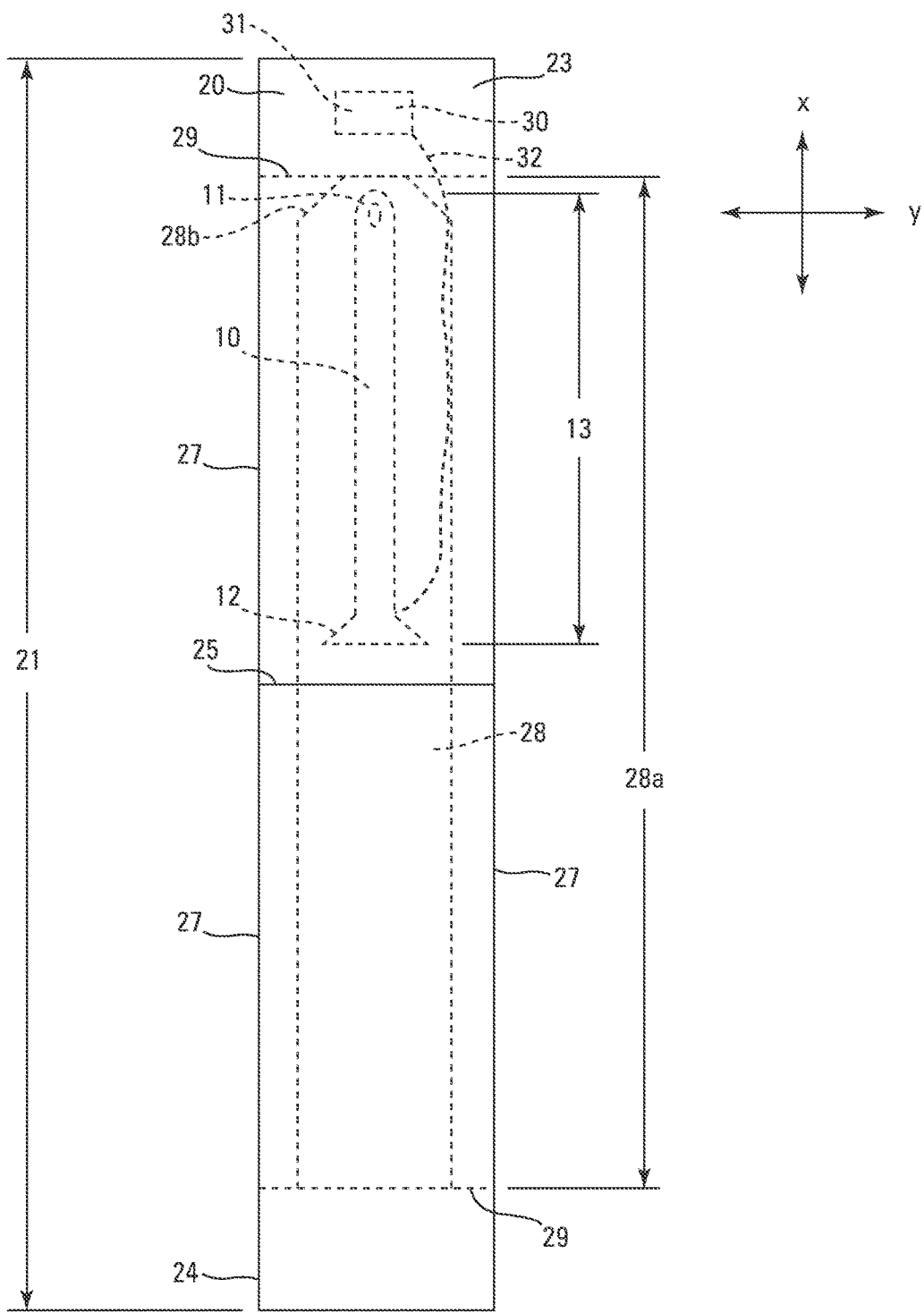
FIG. 1 is a front plan view of one embodiment of a package for an intermittent urinary catheter shown with the package in full longitudinal length.
Figure 6:
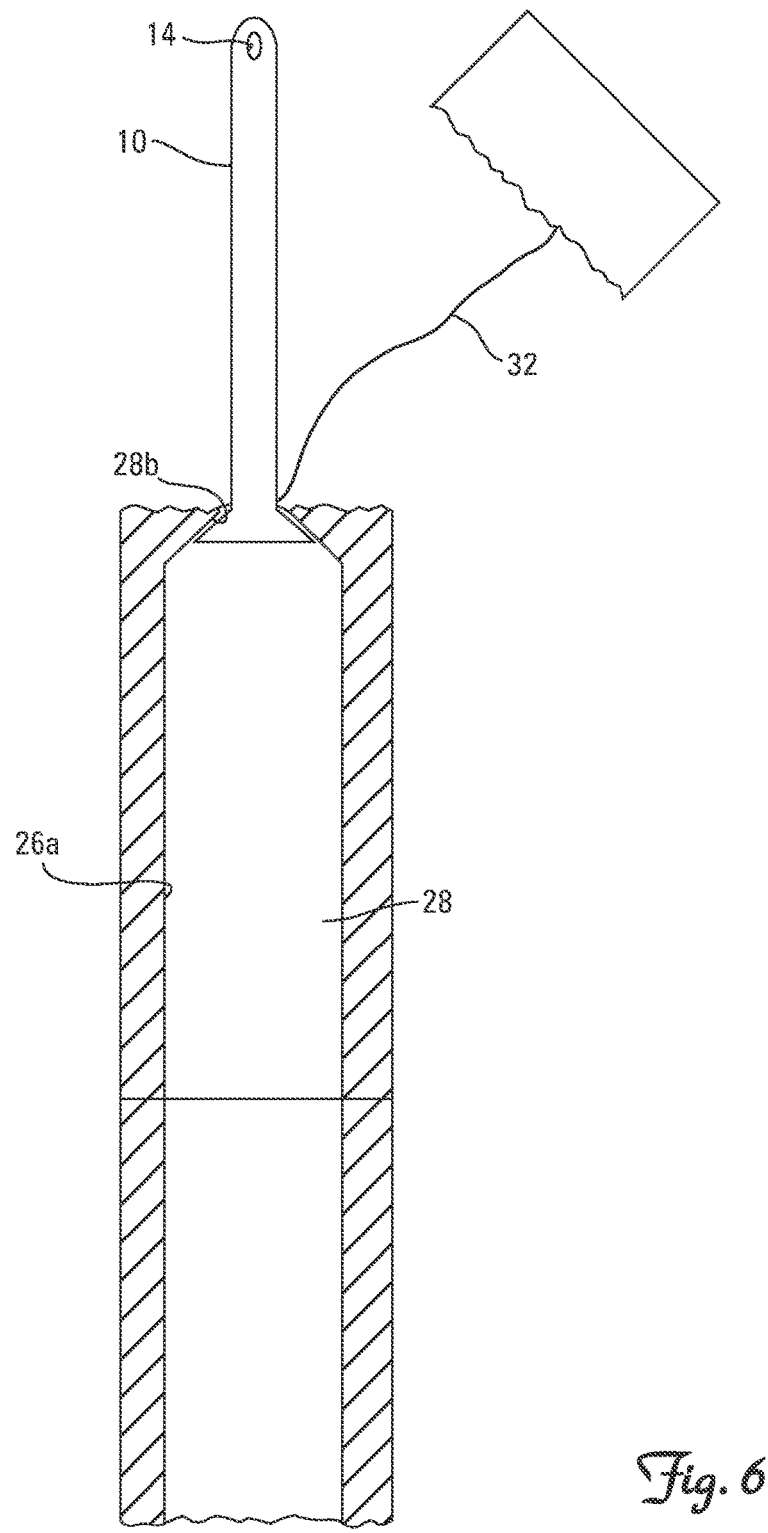
FIG. 6 is a cross-sectional front view of the package shown in FIG. 5 taken along line 5a-5a with the catheter fully extended.

FIG. 1 shows an embodiment of the catheter 10 sterilely packed inside a package 20. The package 20 is shown in full longitudinal length 21. The catheter 10 has at least a distal end 11, a proximal end 12, a longitudinal length 13, a lumen (not numbered), and at least one eyelet 14 (FIG. 6). The distal end 11 is preferably round ended to allow easy and pain free insertion into the urethra of a patient. The distal end 11 has one or more eyelets 14 to accommodate flow of the urine from the bladder through the lumen of the catheter 10. Preferably the eyelets 14 are provided with rounded and or polished rims (not numbered) to increase comfort to the patient during insertion. The proximal end 12 of the catheter 10 provides an exit for the urine from the lumen.

The diameter of the proximal end 12 of the catheter 10 is preferably larger than the diameter of the distal end 11. The proximal end 12 may be any suitable shape to accommodate sliding along the full longitudinal length 21 of the package 20 without exiting the package 20.

The catheter 10 may be coated with a hydrophilic coating to provide a low friction surface when treated with a swelling medium. A swelling medium may be provided within the package 20 to provide a ready to use catheter 10. The use of hydrophilic coating and prepackaged swelling mediums with catheters 10 is well known in the industry. A lubricant may also be provided in the package 20 to provide a low friction surface. Providing a lubricant in a catheter 10 package 20 is well known in the industry.

The catheter 10 may have any desired longitudinal length 13 and shape effective for achieving the function of eliminating urine from the bladder of a male or female patient, including the hollow cylinder or tube shape as shown in FIGS. 1, 4, and 6. Preferably, the longitudinal length 13 for an adult female catheter 10 is between 2-6 inches, the longitudinal length 13 of the adult male catheter 10 is between 10-16 inches, and the longitudinal length 13 of a pediatric catheter 10 is between 5-11 inches.

The catheter 10 may be constructed from any material possessing sufficient structural integrity, being light weight, and having a smooth finish, including specifically, but not exclusively, plastics such as polyethylene, polyvinyl chloride and polyurethane, etc. The catheter 10 may be made without a softening agent also or with a softening agent allowing the catheter 10 to be pliable. Pliability is especially desired for the longer male catheter 10 to allow the catheter 10 to be stiff enough for insertion but to allow enough flexibility to manipulate through the longer urethra of the male anatomy. The catheter 10 may also be elastic like the package 20. Using an elastic catheter 10 would allow the catheter to be compacted to fit into a smaller package 20. An elastic and pliable catheter 10 may decrease the chances of the catheter 10 forming kinks if it is compacted in the package. An elastic catheter 10 may also aid the package 20 in resuming the full longitudinal length 21 upon opening of the package 20.

Preferably the catheter 10 is packaged in an elastic package 20. As shown in FIGS. 2-4 and 9, the package 20 is stored in a compact state defining a compact longitudinal length 22. The package 20 has a compact longitudinal length 22 that is less than the full longitudinal length 21. The elasticity of the package 20 may come from elastic material used to form the package 20 or from a biasing means 70 incorporated into the package 20 wherein the package 20 is biased toward the full longitudinal length 21.

If an elastic material is used to form the package 20, the elasticity of the packaging material biases the package 20 to the full longitudinal length 21. Preferably the package 20 is made from polyester, polyethylene, a combination of the two materials, Surlyn, polyprolene, or aluminum.

Figure 12:
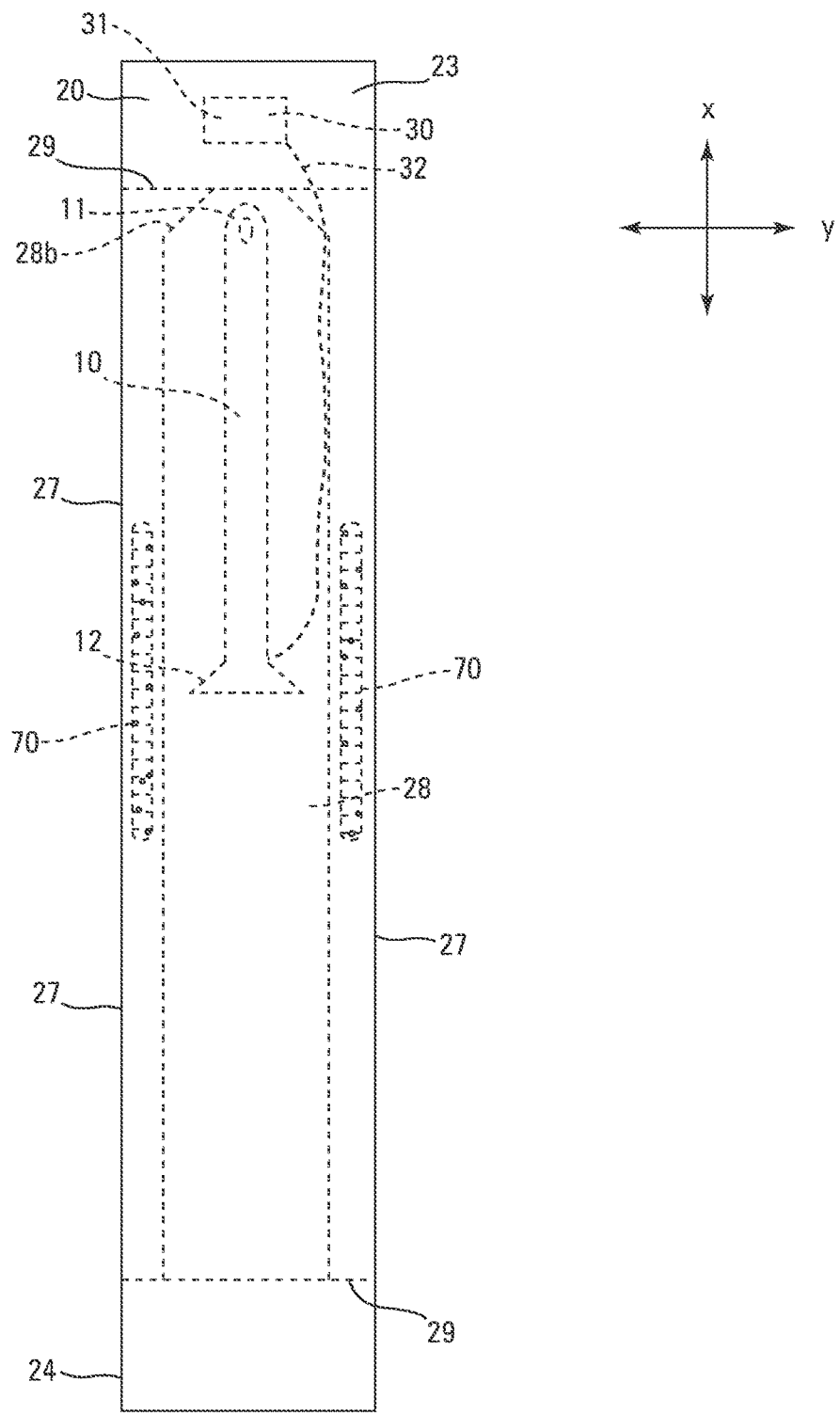
FIG. 12 is a sectional front view of the invention in FIG. 1 with air pockets molded into the package to act as a biasing means.
Figure 13:
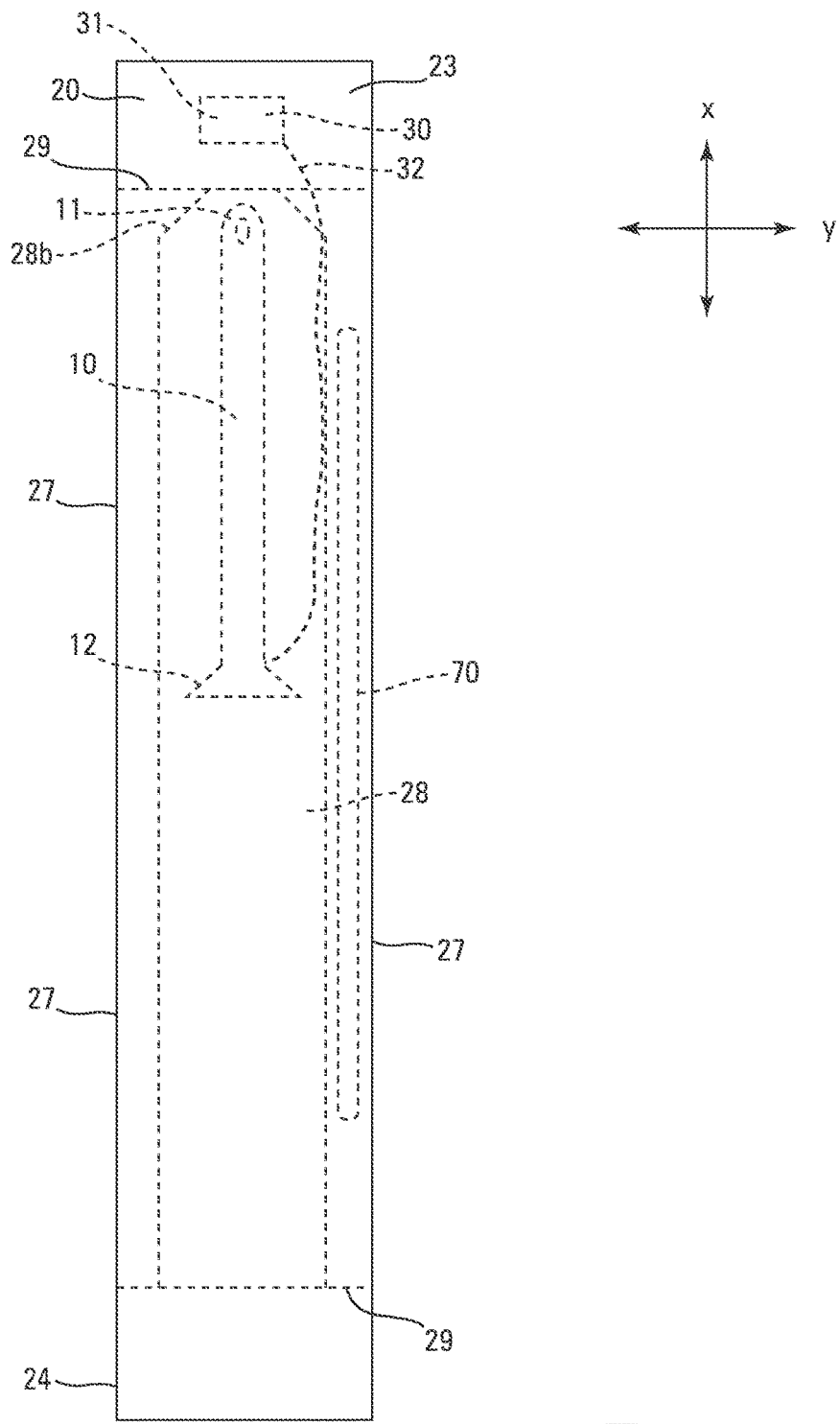
FIG. 13 is a sectional front view of the invention in FIG. 1 with a spring sealed into the package to act as a biasing means.

At least one biasing means 70 may also be used to provide the elasticity of the package 20. Any acceptable biasing means 70 may be used, such as but not exclusively, a spring. As shown in FIGS. 12 and 13, the biasing means 70, is sealed into or molded as part of the package 20. The preferred biasing means 70 is a polymer member or a pressurized chamber. The chamber may be filled with any suitable pressurized fluid such as water or a gas. To increase the elasticity of the package 20 more than one biasing means 70 may be used in a single package 20.

Preferably the inner surface 26a of the package 20 material is smooth to allow for ease in removing the catheter 10 for use and to prevent damage to the catheter 10. FIG. 1 shows the package 20 in a full longitudinal length 21. FIGS. 2-4 and 9 show the package 20 in its compact state where the compact longitudinal length 22 is less than the full longitudinal length 21.

Figure 7A:
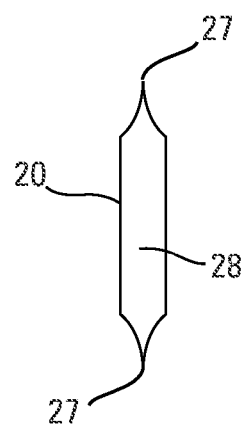
FIG. 7A is a plan end view of the second longitudinal end of the package shown in FIG. 5.
Figure 7B:
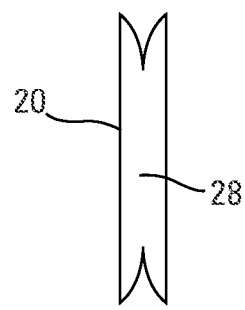
FIG. 7B is a plan end view of an alternative configuration of the second longitudinal end of the package shown in FIG. 5.
Figure 7C:
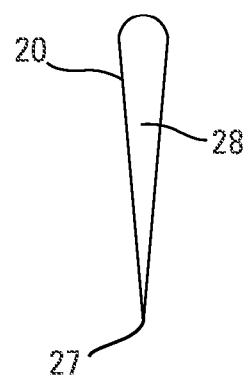
FIG. 7C is a plan end view of a further alternative configuration of the second longitudinal end of the package shown in FIG. 5.

The package 20 has a first longitudinal end 23 and a second longitudinal end 24 and defines an elongate catheter 10 receiving chamber 28 extending along a portion of the full longitudinal length 21 of the package 20. The catheter 10 is carried in the elongate receiving chamber 28 with the distal end 11 of the catheter 10 located proximate the first longitudinal end 23 of the package 20. As shown in FIG. 1, a first embodiment of the package 20 may be constructed from a base sheet of material and cover sheet of material sealed along the edges 27 to form the catheter 10 receiving chamber 28 therein. See FIG. 7A. The first longitudinal end 23 and the second longitudinal end 24 are sealed after insertion of the catheter 10 in the receiving chamber 28. A second embodiment of the package 20 may also be constructed from a single base material folded upon it to provide a single sealed edge 27. See FIG. 7C. The first longitudinal end 23 and second longitudinal end 24 are then sealed after insertion of the catheter 10 in the receiving chamber 28. In a third embodiment, the package 20 may be extruded in a tube shape and then the first longitudinal end 23 and second longitudinal end 24 sealed after insertion of the catheter 10 in the receiving chamber 28. As shown in FIG. 7B, the extruded shape may include longitudinal X creases to allow for flexibility of the package 20 during use.

As shown in FIGS. 1 and 6, the catheter 10 receiving chamber 28 extends from proximate the first longitudinal end 23 of the package 20 to proximate the second longitudinal end 24 of the package 20, as the first longitudinal end 23 and the second longitudinal end 24 are sealed after the catheter 10 is inserted in the receiving chamber 28. The receiving chamber 28 is sized, configured, and arranged to slideably engage the catheter 10. Preferably, proximate the first longitudinal end 23 of the package 20 the size of the receiving chamber 28 is an inwardly directed shoulder 28b effective for decreasing the size of and constricting the receiving chamber 28 such that the shoulder 28b is sized, configured, and arranged to prohibit movement of the proximal end 12 of the catheter 10 from exiting the receiving chamber 28 of the package 20.

Preferably, the package 20 has means to manually remove the first longitudinal end 23 and the second longitudinal end 24 to allow access to the catheter 10 receiving chamber 28. The ends 23 and 24 may have a line of weakness 29 such as perforations or score lines, a tear strip, or a point of weakness to allow easy opening of the package 20 without the need for scissors or a knife. Providing a line of weakness 29 may also direct the patient to open the package 20 at the proper place on the package 20 to allow the proximal end 12 of the catheter 10 to catch on the shoulder 28b of the receiving chamber 28.

As shown in FIGS. 2-4 and 9, the package 20 has a compact longitudinal length 22 that is shorter than the full longitudinal length 21 of the package 20. Preferably the longitudinal length 13 of the catheter 10 is less than the longitudinal length 28a of the receiving chamber 28. If a non-elastic catheter 10 is used this will allow the portion of the package 20 without the catheter 10 to be folded, bent or coiled to form the compacted package 20. It will also provide a longer receiving chamber 28 for use as a drainage tube during use of the catheter 10.

Figure 9:
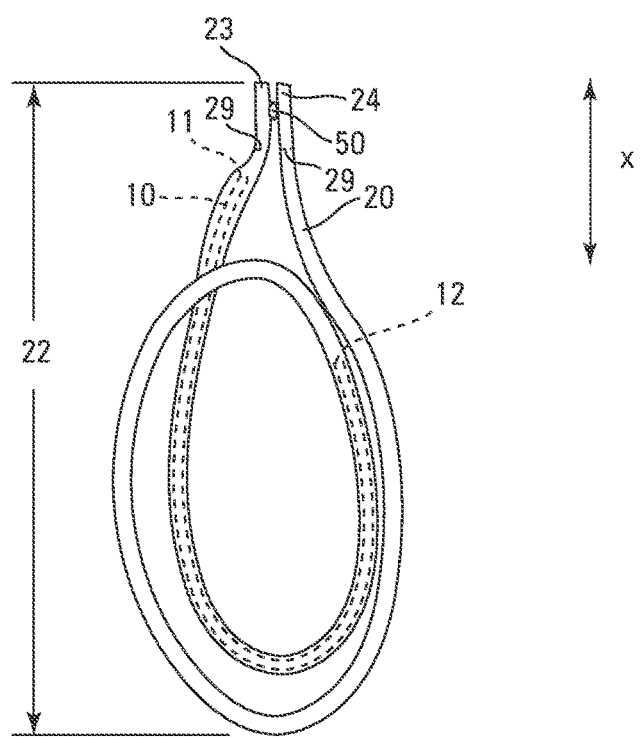
FIG. 9 is a plan side view of a third embodiment of the invention with the package shown in compact longitudinal length.
Figure 10:
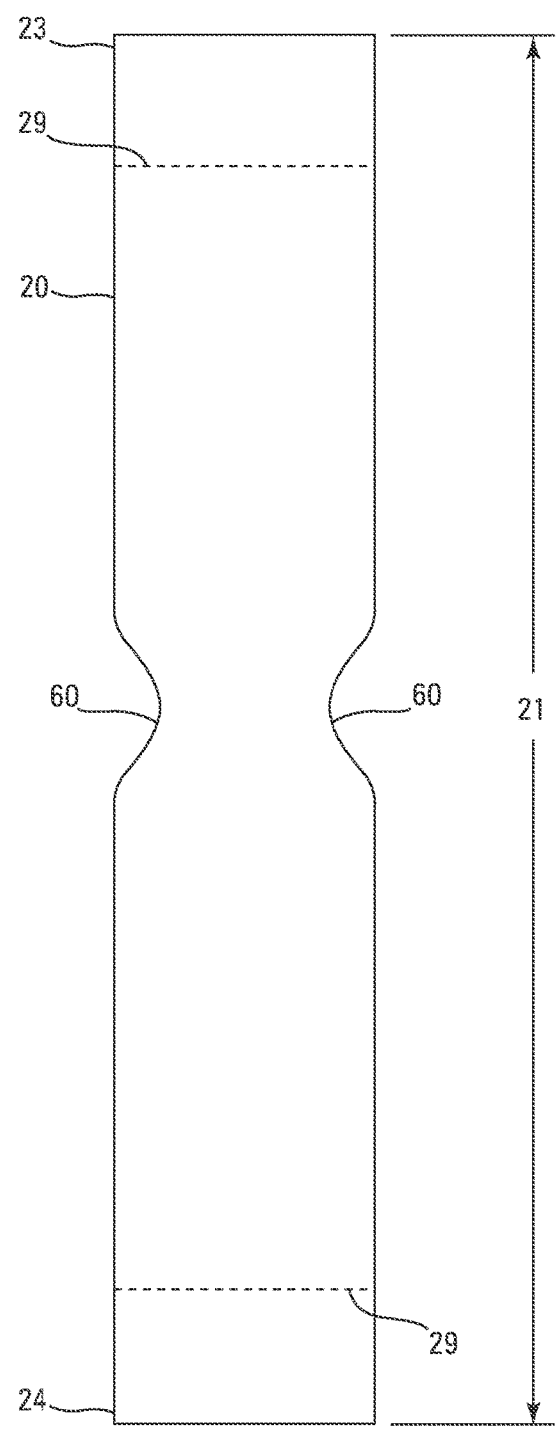
FIG. 10 is a plan front view of a fourth embodiment of the package shown in full longitudinal length.
Figure 11A:
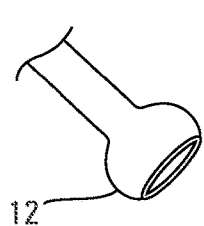
FIG. 11A is a side perspective view of proximal end of the catheter shown In FIG. 6.
Figure 11B:
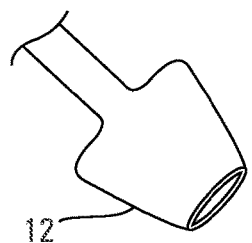
FIG. 11B is a side perspective view of an alternative configuration of the proximal end of the catheter shown in FIG. 6.
Figure 11C:
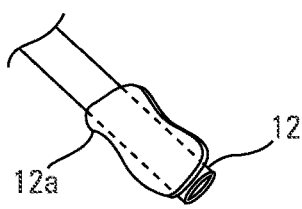
FIG. 11C is a side perspective view of a further alternative configuration of the proximal end of the catheter shown in FIG. 6.
Figure 11D:
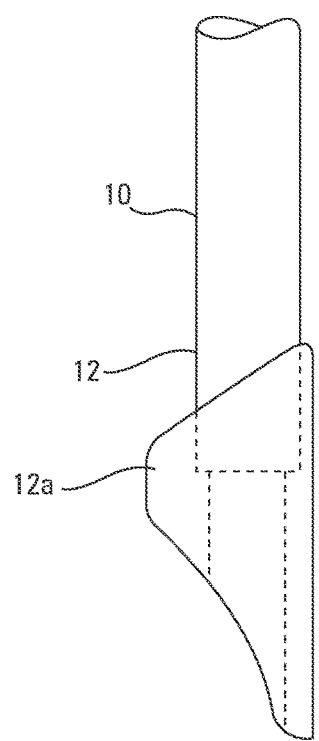
FIG. 11D is a side perspective view of a further alternative configuration of the proximal end of the catheter shown in FIG. 6.
Figure 11E:
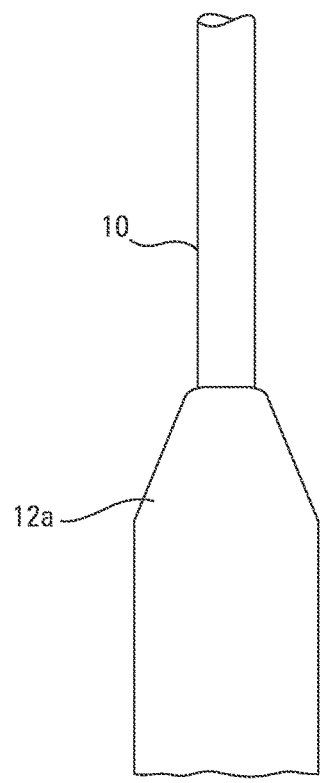
FIG. 11E is a front perspective view of the proximal end of the catheter shown in FIG. 11D.

In the compact longitudinal length 22 the first longitudinal end 23 and the second longitudinal end 24 may be configured and arranged to be removed from the package 20 at the same time by aligning the removal means for each end as shown in FIGS. 3-4 and 9. Preferably the longitudinal ends 23 and 24 are aligned and a fastener 50 used to attach the first end 23 to the second end 24 such that the patient cannot remove the first longitudinal end 23 without removing the second longitudinal end 24. The preferred fastener 50 is an adhesive.

Figure 8:
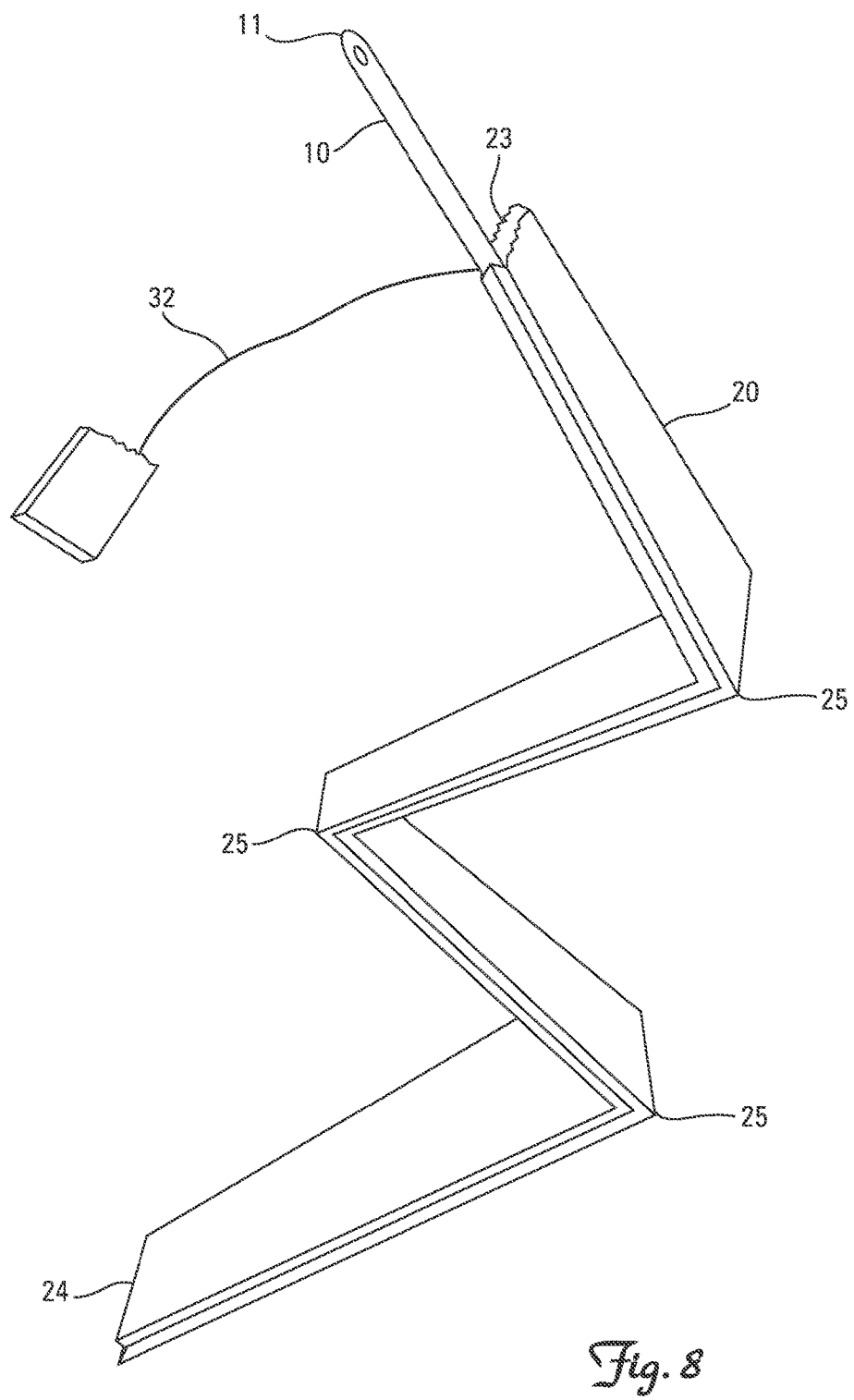
FIG. 8 is a side perspective view of a second embodiment of the package with the first and second longitudinal ends removed and the catheter partially extended.

The package 20 may be converted from the full longitudinal length 21 to the compacted length 22 by folding, coiling, bending, or pleating. As shown in FIGS. 2-4 and 10 the package 20 may be folded or bent a single time. The folding may be made easier by using a hinge 25, score line, or at least one set of laterally Y extending dimples 60 at the point of folding. The hinge 25 may be a live hinge 25 or a mechanical hinge 25. As shown in FIG. 8, the package 20 may be folded or bent more than one time to accommodate a package 20 with a longer full longitudinal length 21. This could allow for a longer drainage tube as well as to accommodate a longer catheter 10. As shown in FIG. 9, the package 20 may be coiled into the compact length 22. Again the package 20 may have one or more coils depending on the original full longitudinal length 21 of the package 20. As the package 20 is elastic, a fastener 50 may be needed to attach the first longitudinal end 23 of the package 20 to the second longitudinal end 24 to keep the package 20 in the compact position. Upon removing the longitudinal ends 23 and 24 of the package 20 or removing the fastener 50 from contact with one of the ends 23 and 24 of the package 20, the package 20 will return to the full longitudinal length 21.

As shown in FIG. 2 the package 20 may also have a mirror 40 on the outer surface 26b to aid the patient in inserting the catheter 10. The package 20 may have a minor like outer surface 26b to aid the patient in inserting the catheter 10.

The package 20 may also have a guide member 30 to aid the patient in removing the distal end 11 of the catheter 10 from the package 20 without touching the catheter 10 and causing contamination. Preferably the guide member 30 has a tab 31 and a tether 32. As shown in FIG. 1, the tab 31, with one end (not numbered) of the tether 32, is attached to the first longitudinal end 23 of the package 20 and the other end (not numbered) of the tether 32 is attached to the distal end 11 of the catheter 10. As shown in FIGS. 1 and 6, the tab 31 may be embedded in the seal of the first longitudinal end 23 of the package 20 wherein removal of the first longitudinal end 23 from the package 20 removes the tab 31 allowing the distal end 11 of the catheter 10 to be pulled out of the package 20 with the tab 31.

Alternatively, the proximal end 12 of the catheter 10 may be configured and arranged to allow the distal end 11 of the catheter 10 to be manually pushed out of the open longitudinal end of the package 20. As shown in FIGS. 1 and 11A-E, the proximal end 12 of the catheter 10 may be attached to or integrally formed with a push block 12a. The push block 12a is shaped to allow a patient to easily grip the proximal end 12 of the catheter 10 through the package 20 and push the distal end 11 of the catheter 10 out of the opened first longitudinal end 23 of the package 20.

Use

The compact packaged intermittent urinary catheter 10 is used by patients for self-catheterization. One or more of the compact packaged catheters 10 may be easily carried by a patient in a purse, bag or pocket. Prior to use the patient should take all sanitary procedures advised by their doctors to decrease the risks of infection from utilizing a catheter 10. The patient grasps the first and second longitudinal ends 23 and 24 of the compact elastic package 20 and removes the ends 23 and 24. The ends 23 and 24 may be removed by cutting with a knife or scissors, but preferably the ends 23 and 24 are removed manually along the lines of weakness 29 or at the point of weakness. As shown in FIGS. 5, 6, and 8, by removing the first longitudinal end 23 and the second longitudinal end 24 at the point of weakness or line of weakness 29, the package 20 will be open such that the receiving chamber 28 are now open. Removing the first longitudinal end 23 of the package 20 too far below the line of weakness 29 or the point of weakness could cause the package 20 to be opened such that the shoulder 28b of the receiving chamber 28 is also removed and proximal end 12 the catheter 10 will no longer be captured within the package 20.

Upon removal of the first and second longitudinal ends 23 and 24 of the package 20, the package 20 is then returned to its full longitudinal length 21.

If the package 20 has a guide member 30, removal of the first longitudinal end 23 of the package 20 will allow the distal end 11 of the catheter 10 to slide from the package 20 without the need to touch or contaminate the catheter 10. If the proximal end 12 of the catheter 10 remains in the receiving chamber 28 of the package 20, the package 20 can be used as a drainage tube for the catheter 10. The catheter 10 is then inserted into the urethra of the patient. As the urine travels through the catheter 10 and exits the proximal end 12 of the catheter 10, it enters the receiving chamber 28 of the package 20 and travels through the longitudinal length 28a of the chamber 28 and out the now open second longitudinal end 24 of the package 20 and into a waste receptacle.

If the catheter 10 has a push block 12a proximate the proximal end 12 of the catheter 10, after the package 20 is opened and the package 20 returns to the full longitudinal length 21, the patient grasps the push block 12a at the proximal end 12 of the catheter 10 through the package 20 and pushes the distal end 11 of the catheter 10 out of the package 20 without touching or contaminating the catheter 10. The catheter 10 may then be used the same as the catheter 10 with the guide member 30.

After the bladder is emptied, the catheter 10 is removed from the urethra and the catheter 10 can be pushed back into the package 20 for easy and mess free disposal.

The compact package described herein may be used to store a sterile catheter packed therein or may be provided along with or separately from the catheter. In either case, the package is preferably used as an aid for inserting the catheter into the urethra. The embodiments described above include the catheter stored in the package which also contains lubricant to assist urethral insertion, or the catheter may be separately inserted into the lubricant-filled package at the time of usage. It should be noted that all of the variations described above pertaining to the way the package is held in a compact shape, or which assist in opening the package to its elongated shape apply equally to the separate package described below. Likewise, other constructional aspects such as materials and dimensions described above may apply equally to the stand-alone package described below.

FIG. 14 is a front perspective view of an alternative form of a package 80 for assisting insertion of an intermittent urinary catheter shown in compact longitudinal length, while FIG. 14A is a cross-sectional side view of the package 80 taken along line 14-14.

The package 80 has a first longitudinal end 82 and a second longitudinal end 84 and defines an elongate catheter receiving chamber 86 extending along a portion of the full longitudinal length of the package 80. As shown in FIG. 14, a first embodiment of the package 80 may be constructed from a base sheet of material and cover sheet of material sealed along side edges 88a and end edge 88b to form the catheter receiving chamber 86 therein. The elongated package 80, best seen in partial view in FIG. 16, folds at a mid-point 90 so that the first and second longitudinal ends 82, 84 meet and are joined into the single end edge 88b. The first longitudinal end 82 and the second longitudinal end 84 are sealed after addition of a lubricating medium in the receiving chamber 86. In a second embodiment the package 80 may be extruded in a tube shape and then the first longitudinal end 82 and second longitudinal end 84 sealed after addition of a lubricating medium in the receiving chamber 86, as in shown in FIG. 7B. A third embodiment of the package 80 may also be constructed from a single base material folded upon it to provide a single sealed edge, as in FIG. 7C.

FIG. 14 also shows a score or notch 92 formed at an outer extent of the sealed side edges 88a at a longitudinal location below the end edge 88b and aligned with the inner chamber 86. An upper portion of the compacted package may be cut away or torn off using the notch 92 as a starter, as seen in FIG. 15, to expose the inner chamber 86 by removing both the first and second longitudinal ends 82, 84. FIG. 16 is a perspective view of the package 80 after removal of the first and second longitudinal ends 82, 84 and in full longitudinal length from a first open end 94 to a second open end 96. Indicator arrows 98 are desirably printed on one or both exterior sides of the elongated package 80 oriented in one longitudinal direction.

FIG. 17 is a perspective view of the elongated package 80 showing a user inserting an intermittent urinary catheter 100 therein in the direction of the indicator arrows 98. The catheter may be any of the various embodiments described above, or other types. A leading end of the catheter is inserted into the first open end 94 and pushed through the chamber 86 having lubricating medium therein.

FIG. 18 shows the intermittent urinary catheter 100 passing completely through the elongated package 80, emerging from the second open end 96. A lubricating medium 102 is seen adhered to an outer surface of the catheter 100 from passing through the catheter-receiving chamber 86.

The package 80 is then used to assist in inserting the catheter 100 into a urethra. FIG. 19 is a perspective view like FIG. 18 showing the user holding the package 80 with the intermittent urinary catheter 100 therein in preparation for use. A portion of the leading end 104 of the catheter 100 with lubricant 102 thereon extends from the second open end 96. The user can easily and cleanly grasp the side of the elongated package 80 to manipulate the leading end 104 into the proper position. Once the leading end 104 is inserted into the urethra, the user can maintain a grip on the catheter 100 as it is advanced in stages, with the package 80 sliding back over the catheter so as to continue to lubricate its length. When the process is complete, the package 80 again can be used to grip and remove the catheter 100 from the urethra.

The stand-alone package 80 described above is easy and convenient to use with a variety of different catheters. Often, with simple ketchup-style gel packages used to deposit lubricant on the catheter the gel coating can be lumpy and inconsistent. With the catheter 100 passing through the package chamber 86, the gel is instead applied evenly and smoothly. Further, the user's fingers remain outside the package 80 at all times so there is no mess. The package 80 acts as a clean handling sleeve for both advancing and retracting the catheter. The package 80 is relatively simple and economical, making it an advantageous way to facilitate the often messy job of urinary catheter insertion.

Throughout this description, the embodiments and examples shown should be considered as exemplars, rather than limitations on the apparatus and procedures disclosed or claimed. Although many of the examples presented herein involve specific combinations of method acts or system elements, it should be understood that those acts and those elements may be combined in other ways to accomplish the same objectives. Acts, elements and features discussed only in connection with one embodiment are not intended to be excluded from a similar role in other embodiments.

It is claimed:

1. A compact package for an intermittent urinary catheter, comprising:
    a flexible package having an open extended state between opposite first and second longitudinal ends and defining a first longitudinal length, the flexible package also having a closed compacted state wherein the first and second longitudinal ends are aligned and adhered together and a mid-portion of the flexible package is coiled or folded so that the flexible package defines a second longitudinal length of one half or less of the first longitudinal length,
    the flexible package defining a longitudinally extending receiving chamber between the first and second longitudinal ends containing a lubricating medium,
    wherein the first and second longitudinal ends are aligned and adhered together to seal the receiving chamber such that the first longitudinal end cannot be removed without removing the second longitudinal end, and wherein removing both the first and second longitudinal ends unseals and opens the receiving chamber at both longitudinal ends and enables conversion of the flexible package from its closed compacted state to its open extended state by unfolding or uncoiling the mid-portion,
    the flexible package further having a weak point to assist in tearing or cutting off the first and second longitudinal ends, and
    wherein the receiving chamber is sized and configured when the package is in its open extended state to slidably receive a longitudinally elongated intermittent urinary catheter so that the lubricating medium coats the catheter exterior.

2. The compact package, as set forth in claim 1, wherein the weak point is selected from the group consisting of a notch and a score line.

3. The compact package, as set forth in claim 1, wherein the compacted state of the package includes a single fold in the mid-portion with the first and second longitudinal ends being joined together opposite the single fold.

4. The compact package, as set forth in claim 3, wherein the package has at least one set of laterally extending dimples aligned with the single fold to allow the package to be folded into its compacted state.

5. The compact package, as set forth in claim 1, wherein the compacted state of the package includes a coiled mid-portion with the first and second longitudinal ends being joined together opposite the coiled mid-portion.

6. The compact package, as set forth in claim 1, wherein the package has a biasing means extending across the coiled or folded mid-portion so as to bias the package toward its extended state.

7. The compact package, as set forth in claim 1, wherein the compacted state of the package includes a pleated mid-portion with multiple folds with the first and second longitudinal ends being joined together opposite the pleated mid-portion.

8. The compact package, as set forth in claim 7, wherein the biasing means is a polymer member.

9. The compact package, as set forth in claim 7, wherein the biasing means is at least one pressurized chamber.

10. The compact package, as set forth in claim 1, further including a mirror on an outer surface thereof to aid the patient in inserting the catheter.

11. A compact package for an intermittent urinary catheter, comprising:
    a flexible package having an open extended state between opposite first and second longitudinal ends and defining a first longitudinal length, the flexible package also having a closed compacted state wherein the first and second longitudinal ends are aligned and adhered together and a mid-portion of the flexible package is coiled or folded so that the flexible package defines a second longitudinal length of one half or less of the first longitudinal length, the flexible package defining a longitudinally extending receiving chamber between the first and second longitudinal ends containing a lubricating medium, wherein the first and second longitudinal ends are aligned and adhered together to seal the receiving chamber such that the first longitudinal end cannot be removed without removing the second longitudinal end, and wherein removing both the first and second longitudinal ends unseals and opens the receiving chamber at both longitudinal ends and enables conversion of the flexible package from its closed compacted state to its open extended state by unfolding or uncoiling the mid-portion, the flexible package further having a weak point to assist in tearing or cutting off the first and second longitudinal ends, a longitudinally elongated intermittent urinary catheter sealed within the receiving chamber having a proximal end and at least one eyelet on a rounded distal end, and wherein the distal end of the longitudinally elongated intermittent urinary catheter may be urged from within the receiving chamber after the first and second longitudinal ends of the package are removed.

12. The compact package, as set forth in claim 11, further comprising a guide member attached to the first longitudinal end of the package and having a tether attached to the urinary catheter wherein removal of the first longitudinal end of the package slideably pulls the catheter from the package without contamination of the catheter.

13. The compact package, as set forth in claim 11, wherein proximate the first longitudinal end of the package the receiving chamber has an inwardly directed shoulder effective for decreasing the size of the receiving chamber wherein the shoulder is sized, configured, and arranged to prohibit the movement of the proximal end of the urinary catheter which is enlarged from exiting the receiving chamber.

14. The compact package, as set forth in claim 13, wherein a proximal end of the urinary catheter has a push block to enable a distal end of the catheter to be manually pushed out of the receiving chamber after opening the receiving chamber by manipulating the push block through the package.

15. The compact package, as set forth in claim 11, wherein the urinary catheter is elastic and pliable and is arranged across the coiled or folded mid-portion.

16. The compact package, as set forth in claim 11, wherein the urinary catheter lies straight within only a portion of the receiving chamber in the closed compacted state of the package and does not cross the coiled or folded mid-portion.

17. The compact package, as set forth in claim 11, wherein the weak point is selected from the group consisting of a notch and a score line.

18. The compact package, as set forth in claim 11, wherein the compacted state of the package forms a shape selected from the group consisting of a single fold in the mid-portion, a pleated mid-portion with multiple folds and a coiled mid-portion.

19. The compact package, as set forth in claim 11, wherein the package has a biasing means extending across the coiled or folded mid-portion so as to bias the package toward its extended state.

20. The compact package, as set forth in claim 11, wherein the at least one eyelet is provided with rounded and or polished rims.

* * * * *